US006991627B2

(12) United States Patent
Madhani et al.

(10) Patent No.: US 6,991,627 B2
(45) Date of Patent: Jan. 31, 2006

(54) ARTICULATED SURGICAL INSTRUMENT FOR PERFORMING MINIMALLY INVASIVE SURGERY WITH ENHANCED DEXTERITY AND SENSITIVITY

(75) Inventors: Akhil J. Madhani, Cambridge, MA (US); J. Kenneth Salisbury, Cambridge, MA (US)

(73) Assignee: Intuitive Surgical Inc., Sunnyvale, CA (US)

( * ) Notice: Subject to any disclaimer, the term of this patent is extended or adjusted under 35 U.S.C. 154(b) by 478 days.

(21) Appl. No.: 10/076,812

(22) Filed: Feb. 15, 2002

(65) Prior Publication Data

US 2002/0103476 A1 Aug. 1, 2002

Related U.S. Application Data

(63) Continuation of application No. 09/340,946, filed on Jun. 28, 1999, which is a continuation of application No. 09/030,661, filed on Feb. 25, 1998, now Pat. No. 5,976,122, which is a continuation of application No. 08/857,776, filed on May 16, 1997, now Pat. No. 5,792,135.

(60) Provisional application No. 60/017,981, filed on May 20, 1996.

(51) Int. Cl.
*A61B 17/00* (2006.01)
(52) U.S. Cl. .................. 606/1; 606/170; 74/490.05; 74/490.06
(58) Field of Classification Search .............. 606/1, 606/130, 170; 74/490.05, 490.06; 600/102, 600/109; 414/1
See application file for complete search history.

(56) References Cited

U.S. PATENT DOCUMENTS

| 1,620,828 A | 3/1927 | Molony |
| 4,762,455 A | 8/1988 | Coughlan et al. |
| 4,921,393 A | 5/1990 | Andeen et al. |

(Continued)

FOREIGN PATENT DOCUMENTS

WO WO 97/29690 8/1997

(Continued)

OTHER PUBLICATIONS

Alexander, III, Arthur D., "Impacts of Telemation on Modern Society," *Symposium on Theory and Practice of Robots and Manipulators*, vol. II, pp. 122-136 (Sep. 5-8, 1973).

(Continued)

*Primary Examiner*—Julian W. Woo
(74) *Attorney, Agent, or Firm*—Lynn Thompson; Townsend Townsend & Crew

(57) ABSTRACT

An articulated surgical instrument for enhancing the performance of minimally invasive surgical procedures. The instrument has a high degree of dexterity, low friction, low inertia and good force reflection. A unique cable and pulley drive system operates to reduce friction and enhance force reflection. A unique wrist mechanism operates to enhance surgical dexterity compared to standard laparoscopic instruments. The system is optimized to reduce the number of actuators required and thus produce a fully functional articulated surgical instrument of minimum size.

75 Claims, 8 Drawing Sheets

U.S. PATENT DOCUMENTS

| | | | | |
|---|---|---|---|---|
| 5,078,140 | A | | 1/1992 | Kwoh |
| 5,178,032 | A | | 1/1993 | Zona et al. |
| 5,209,747 | A | | 5/1993 | Knoepfler |
| 5,217,003 | A | * | 6/1993 | Wilk ........................... 600/109 |
| 5,254,130 | A | | 10/1993 | Poncet et al. |
| 5,312,399 | A | | 5/1994 | Hakky et al. |
| 5,313,962 | A | | 5/1994 | Obenchain |
| 5,339,799 | A | | 8/1994 | Kami et al. |
| 5,368,015 | A | | 11/1994 | Wilk |
| 5,374,277 | A | | 12/1994 | Hassler |
| 5,417,210 | A | | 5/1995 | Funda et al. |
| 5,441,494 | A | | 8/1995 | Ortiz |
| 5,454,827 | A | | 10/1995 | Aust et al. |
| 5,456,684 | A | | 10/1995 | Schmidt et al. |
| 5,528,955 | A | | 6/1996 | Hannaford et al. |
| 5,556,401 | A | | 9/1996 | Caillouette |
| 5,558,668 | A | | 9/1996 | Lankford et al. |
| 5,626,595 | A | * | 5/1997 | Sklar et al. .................. 606/170 |
| 5,762,458 | A | * | 6/1998 | Wang et al. .................... 414/1 |
| 5,800,423 | A | * | 9/1998 | Jensen ........................... 606/1 |
| 5,808,665 | A | | 9/1998 | Green |
| 5,876,325 | A | * | 3/1999 | Mizuno et al. ............. 600/102 |

FOREIGN PATENT DOCUMENTS

| | | |
|---|---|---|
| WO | WO 00/67640 A2 | 11/2000 |

OTHER PUBLICATIONS

Bejczy, A.K. et al., "Controlling Remote Manipulators Through Kinesthetic Coupling," *Computers in Mechanical Engineering*, pp. 48-60 (Jul. 1983).

Fukuda, T. et al., "Micro Active Catheter System With Multi Degrees of Freedom," 1994 IEEE International Conference on Robotics and Automation, 1994 Proceedings, vol. 3, pp. 2290-2295.

Neisius, B. et al., "Robitic Telemanipulator for Laparoscopy," Annual International Conference of the IEEE Engineering in Medicine and Biology— Proceedings of the 1995 IEEE Engineering in Medicine and Biology $17^{th}$ Annual Conference and 21 Canadian Medical and Biological Engineering Conference, Sep. 20-23, 1995, vol. 17, No. 2.

Schenker, P.S. et al., Development of Telemanipulator for Dexterity Enhanced Microsurgery, Second Annual International Symposium on Medical Robotics and Computer Assisted Surgery, Nov. 4-7, 1995 (Marriott Inner Harbor Hotel, Baltimore, Ms. Daunt), pp. 81-88.

Taubes, Gary, "Surgery in Cyberspace," *Discover*, pp. 85-92 (Dec. 1994).

* cited by examiner

ARTICULATED SURGICAL INSTRUMENT FOR PERFORMING MINIMALLY INVASIVE SURGERY WITH ENHANCED DEXTERITY AND SENSITIVITY

CROSS-REFERENCES TO RELATED APPLICATIONS

This application is a continuation of, and claims the benefit of priority from, U.S. patent application Ser. No. 09/340,946, filed Jun. 28, 1999, which is a continuation of U.S. patent application Ser. No. 09/030,661, filed Feb. 25, 1998 (now U.S. Pat. No. 5,976,122), which is a continuation of U.S. patent application Ser. No. 08/857,776, filed May 16, 1997 (now U.S. Pat. No. 5,792,135), which claims priority to U.S. Provisional Application No. 60/017,981, filed May 20, 1996, the full disclosures of which are incorporated herein by reference.

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

1. Field of the Invention

This invention relates generally to methods and apparatus for enhancing the performance of minimally invasive surgery. This invention relates particularly to surgical instruments that augment a surgeon's ability to perform minimally invasive surgical procedures. This invention relates more particularly to a novel articulated surgical instrument for minimally invasive surgery which provides a high degree of dexterity, low friction, low inertia and good force reflection.

2. Background of the Invention

Minimally invasive medical techniques are aimed at reducing the amount of extraneous tissue which must be damaged during diagnostic or surgical procedures, thereby reducing patient recovery time, discomfort, and deleterious side effects. Approximately 21,000,000 surgeries are now performed each year in the United States. It is estimated that 8,000,000 of these surgeries can potentially be performed in a minimally invasive manner. However, only about 1,000,000 surgeries currently use these techniques due to limitations in minimally invasive surgical instruments and techniques and the additional surgical training required to master them.

Advances in minimally invasive surgical technology could have a dramatic impact. The average length of a hospital stay for a standard surgery is 8 days, while the average length for the equivalent minimally invasive surgery is 4 days. Thus, the complete adoption of minimally invasive techniques could save 28,000,000 hospital days, and billions of dollars annually in hospital residency costs alone. Patient recovery times, patient discomfort, surgical side effects, and time away from work are also reduced with minimally invasive surgery.

The most common form of minimally invasive surgery is endoscopy. Probably the most common form of endoscopy is laparoscopy which is minimally-invasive inspection and surgery inside the abdominal cavity. In standard laparoscopic surgery, a patient's abdomen is insufflated with gas, and cannula sleeves are passed through small (approximately ½ inch) incisions to provide entry ports for laparoscopic surgical *instruments*.

The laparoscopic surgical instruments generally include a laparoscope for viewing the surgical field, and working tools such as clamps, graspers, scissors, staplers, and needle holders. The working tools are similar to those used in conventional (open) surgery, except that the working end of each tool is separated from its handle by an approximately 12-inch long extension tube.

To perform surgical procedures, the surgeon passes instruments through the cannula and manipulates them inside the abdomen by sliding them in and out through the cannula, rotating them in the cannula, levering (i.e., pivoting) the instruments in the abdominal wall and actuating end effectors on the distal end of the instruments. The instruments pivot around centers of rotation approximately defined by the incisions in the muscles of the abdominal wall. The surgeon monitors the procedure by means of a television monitor which displays the abdominal worksite image provided by the laparoscopic camera.

Similar endoscopic techniques are employed in arthroscopy, retroperitoneoscopy, pelviscopy, nephroscopy, cystoscopy, cisternoscopy, sinoscopy, hysteroscopy and urethroscopy. The common feature of all of these minimally invasive surgical techniques is that they visualize a worksite within the human body and pass specially designed surgical instruments through natural orifices or small incisions to the worksite to manipulate human tissues and organs thus avoiding the collateral trauma caused to surrounding tissues which would result from creating open surgical access.

There are many disadvantages of current minimally invasive surgical technology. For example, existing MIS instruments deny the surgeon the flexibility of tool placement found in open surgery. Most laparoscopic tools have rigid shafts and are constrained to approach the worksite from the direction of the small incision. Additionally, the length and construction of many endoscopic instruments reduces the surgeon's ability to feel forces exerted by tissues and organs on the end effector of the tool. The lack of dexterity and sensitivity provided by endoscopic tools is a major impediment to the expansion of minimally invasive surgery.

Telesurgery systems for use in surgery are being developed to increase a surgeon's dexterity as well as to allow a surgeon to operate on a patient from a remote location. Telesurgery is a general term for surgical systems where the surgeon uses some form of servomechanism to manipulate the surgical instruments movements rather than directly holding and moving the tools. In a system for telesurgery, the surgeon is provided with an image of the patient's body at the remote location. While viewing the threedimensional image, the surgeon performs the surgical procedures on the patient by manipulating a master device which controls the motion of a servomechanism-actuated instrument. The surgeon's hands and the master device are positioned relative to the image of the operation site in the same orientation as the instrument is positioned relative to the act. During the operation, the instrument provides mechanical actuation and control of a variety of surgical instruments, such as tissue graspers, needle drivers, etc., that each perform various functions for the surgeon, i.e., holding or driving a needle, grasping a blood vessel or dissecting tissue.

Such telesurgery systems have been proposed for both open and endoscopic procedures. An overview of the state of the art with respect to telesurgery technology can be found in "Computer Integrated Surgery: Technology And Clinical Applications" (MIT Press, 1996). Moreover, prior systems for telesurgery are described in U.S. Pat. Nos. 5,417,210, 5,402,801, 5,397,323, 5,445,166, 5,279,309, 5,299,288.

However methods of performing telesurgery using telemanipulators still require the development of dexterous surgical instruments capable of transmitting position, force, and tactile sensations from the surgical instrument back to the surgeon's hands as he/she operates the telesurgery system such that the system the surgeon has the same feeling as if manipulating the surgical instruments directly by hand. A system's ability to provide force reflection is limited by factors such as friction within the mechanisms, gravity, the inertia of the surgical instrument and forces exerted on the instrument at the surgical incision.

What is needed, therefore, is a surgical instrument that increases the dexterity with which a surgeon can perform minimally invasive surgical procedures.

It would also be desirable to provide a dexterous surgical apparatus having a wrist with two degrees-of-freedom.

It would further be desirable to provide a wrist mechanism that has low friction in order to provide the surgeon with sensitive feedback of forces exerted on the surgical instrument.

It would still further be desirable to provide a surgical instrument having a wrist mechanism for minimally invasive surgery which is suitable for operation in a telemanipulator mechanism.

BRIEF SUMMARY OF THE INVENTION

Accordingly, it is an object of this invention to provide a surgical instrument that increases the dexterity with which a surgeon can perform minimally invasive surgical procedures.

It is also an object of this invention to provide a dexterous surgical apparatus having a wrist with two degrees-of-freedom.

It is a further object of this invention to provide a wrist mechanism that has low friction in order to provide the surgeon with sensitive feedback of forces exerted on the surgical instrument.

It is a still further object of this invention to provide a surgical instrument having a wrist mechanism for minimally invasive surgery which is suitable for operation in a telemanipulator mechanism.

In accordance with the above objects of the invention applicants describe a compact articulated surgical instrument suitable for endoscopic surgery. The instrument has two opposed pivoting jaws and a pivoting wrist member. The instrument is capable of providing force reflection with high sensitivity. The instrument is adapted to be coupled via a servomechanism to a master control operated by a surgeon.

BRIEF DESCRIPTION OF THE DRAWINGS

The foregoing and other objects, features and advantages of the invention will be apparent from the following more particular description of preferred embodiments of the drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
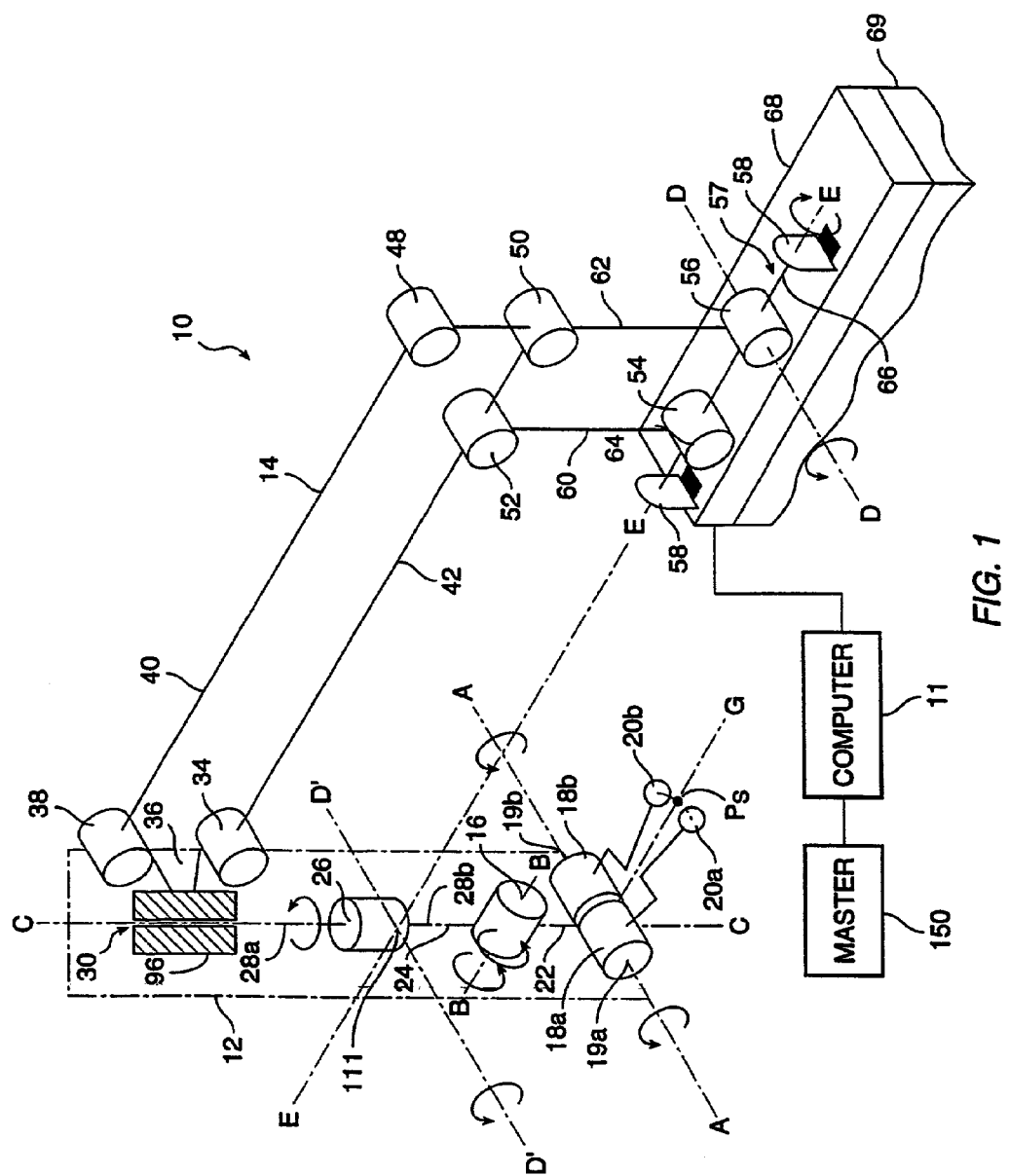
FIG. 1 is a schematic drawing of a servomechanical surgery system including a force-reflecting surgical instrument mounted to a positioning mechanism.

The surgical instrument in the first embodiment includes an elongate support member having a proximal portion and a distal portion lying along a longitudinal axis. A distal wrist member is rotatably coupled to the distal portion of the support member by a wrist joint. First and second opposed work members are mounted to respective first and second driven capstans. The first and second driven capstans are rotatably mounted to the wrist member by respective first and second capstan joints which preferably have a common axis. First, second, third and fourth intermediate idler pulleys are rotatably mounted to the wrist member about the wrist joint. A cable drive system including first, second, third and fourth cables is provided. Each intermediate idler pulley is engaged by one cable and each driven capstan is drivingly engaged by two cables. The cable drive system is capable of pivoting the wrist member about the wrist joint and pivoting the work members independently of each other about the capstan joints.

In preferred embodiments, a linear bearing is mounted in sliding engagement with the support member for allowing the distal portion of the support member to be reciprocated along the longitudinal axis relative to the proximal portion of the support member. In such embodiments the cable drive system is capable of translating the support member along the longitudinal axis. In preferred embodiments, the support member may also include a rotary joint separating the proximal and distal portions of the support member for allowing rotation of the distal portion relative to the proximal portion about the longitudinal axis. In such embodiments the first through fourth cables are capable of twisting about the longitudinal axis during rotation of the distal portion and the cable drive system comprises a fifth cable coupled to the rotary joint for rotating the distal portion about the longitudinal axis.

The present invention also provides a novel system for tensioning the first, second, third and fourth cables. A first proximal idler pulley rotatably engages and tensions the first and second cables. A second proximal idler pulley rotatably engages and tensions the third and fourth cables. Fifth and sixth cables are connected to the first and second proximal idler pulleys for tensioning the first and second proximal idler pulleys. A third more proximal idler pulley is rotatably mounted to a support member for rotatably engaging and tensioning the fifth and sixth cables.

The surgical instrument further includes a plurality of actuators, each for driving one of the cables of the cable drive system. The instrument preferably comprises one actuator for each degree-of-freedom of the instrument. The actuators are preferably servomotors which are positioned between the intermediate idler pulleys and the proximal idler pulleys. The servomotors are preferably directly coupled to the cables by means of a drive capstan mounted on the drive shaft of the servomotor.

The surgical instrument is adapted to be a slave device which is controlled by a master device and a controller. Movements of the instrument and the master device as well as forces exerted thereon may be scaled between the instrument and the master device. A positioning mechanism having two degrees-of-freedom may be mounted to the instrument for positioning the instrument over a work site. The positioning mechanism may provide the instrument with redundant degrees-of-freedom for positioning the endpoint. The combination of a positioning mechanism with the applicants articulated surgical instrument is adapted to enable a surgeon operating the master device to feel forces that are experienced by the instrument during positioning and use of the instrument with greater sensitivity than with prior systems.

Details about the preferred attributes of the surgical system are also described in applicants' copending applications titled "Force-Reflecting Surgical Instrument And Positioning Mechanism For Performing Minimally Invasive Surgery With Enhanced Dexterity And Sensitivity" and "Wrist Mechanism For Surgical Instrument For Performing Minimally Invasive Surgery With Enhanced Dexterity And Sensitivity" filed on even date herewith. The disclosures of these applications are incorporated herein by reference.

Referring to FIG. 1, telesurgery system 10 allows a surgeon at one location to perform surgery on a patient at another location. The surgeon may be in the same operating room as the patient or many miles away. Telesurgery system 10 includes a force-reflecting surgical instrument 12 which is mounted by a bracket 36 to a positioning mechanism 14. Instrument 12 and positioning mechanism 14 are controlled by a computer 11 and a master device 150 which is manipulated by a surgeon at a remote location. Instrument 12 and positioning mechanism 14 are driven by drive motors M1, M2, M3, M4, M5, M6 and M7 (FIGS. 3, 4, 6 and 7a–b) in conjunction with a series of cables and pulleys.

Instrument 12 has low friction, low inertia and high bandwidth but a small range of motion. Positioning mechanism 14 has a large range of motion but typically has a higher inertia and a lower bandwidth than the instrument. The combination of instrument 12 and positioning mechanism 14 in a macro/micro actuation scheme results in a system with increased dynamic range compared to either of its individual components. Positioning mechanism 14 provides telesurgery system 10 with redundant degrees-of-freedom and helps positions instrument 12 at a surgical worksite so that instrument 12 is generally in the proper location for performing the necessary surgery. Thus, by mounting instrument 12 on positioning mechanism 14, telesurgery system 10 is provided with high quality force control through the use of instrument 12 while at the same time having a large range of motion due to positioning mechanism 14. Instrument 12 is mounted on positioning mechanism by means of mounting bracket 36. Preferably, the Instrument 12 is releasably attached to positioning mechanism 14 using any suitable releasable attachment means such as screws, bolts, clamps.

Instrument 12 has a proximal portion 28a which is rotatably coupled to a distal portion 28b by a rotary joint 26. Proximal portion 28a is slidably coupled to a sliding bracket 96 which forms a sliding joint 30. Sliding bracket 96 is fixed to bracket 36. Bracket 36 is a mounting bracket which releasably connects instrument 12 to positioning mechanism 14. Distal portion 28b of instrument 12 includes a wrist member which is rotatably coupled to a tubular support member 24 by a wrist joint 16. Two opposed work members 20a and 20b are fixed to respective driven capstans 18a and 18b which are rotatably coupled to wrist member 22 about capstan joints 19a and 19b. The work members 20a and 20b can be the operative end of standard surgical instruments such as scissors, retractors, needle drivers and electrocautery instruments.

Instrument 12 has five degrees-of-freedom with sliding joint 30 providing linear motion along longitudinal axis C—C, rotary joint 26 providing rotational motion about axis C—C, wrist joint 16 providing rotational motion about axis B—B and capstan joints 19a and 19b providing rotational motion about axis A—A for work members 20a and 20b. Instrument 12 provides master device 150 with four degrees of force reflection so that the surgeon can have tactile feedback of surgical procedures. These degrees of force reflection include x, y and z forces exerted on the work members 20a and 20b, as well as the holding force between work members 20a and 20b. However, force reflection can be provided on more or fewer motion axes as required in any particular embodiment.

Positioning mechanism 14 is a two degree-of-freedom linkage which is preferably a four bar linkage which rotates about an axis E—E. Positioning mechanism 14 has a series of rigid members 36, 40, 42, 60 and 62 which are joined together by joints 34, 38, 48, 50, 52, 54, 56. Positioning mechanism 14 also includes a base 68 having ears 58 which engage shafts 64 and 66 to form a joint 57 for pivoting about axis E—E. Joint 56 allows link 62 to rotate about axis D—D which is orthogonal to axis E—E. The four bar linkage of rigid members 36, 40, 42, 60 and 62 transmits this rotation to instrument 12 via bracket 36 causing instrument 12 to rotate about axis E—E and axis D'—D'(axis D'—D'is parallel to axis D—D and intersects axis E—E orthogonally). Thus the four bar linkage operates to move point $P_S$ of instrument 12 about the surface of a sphere having its center at a remote center 111. Although a four bar linkage has been shown, the articulated surgical instrument of the present invention can be supported by any suitable positioning mechanism. To be suitable for minimally invasive surgery the positioning mechanism must pivot the surgical instrument about axes that intersect at the orifice through which the instrument is inserted into the patient.

Haptic master device 150 suitable to control instrument 12 is a seven degree-of-freedom input device. During use the master 150 is fixed in place to a console or cart or similar stationary support such that the mount provides a fixed reference point. During use, the surgeon manipulates the position and orientation of the master mechanism relative to its stationary support. Linkages, motors and encoders of the master detect the surgeon's movements and transmit them to the computer. The motors of the master preferably also provide force feedback to the surgeon. This controls motions of instrument 12 and positioning mechanism 14 and thus controls the position of the distal end of instrument 12 relative to the surgical site.

One apparatus suitable for use as a master in the presently described system is described in U.S. Pat. No. 5,587,937, titled Force Reflecting Haptic Interface the contents of which are incorporated by reference herein. Another suitable master device is described in U.S. Pat. No. 5,576,727, titled Electromechanical Human-Computer Interface With Force-Feedback the contents of which are incorporated by reference herein. The haptic master apparatus disclosed in the above references would require the addition of a further powered degree-of-freedom to provide force reflection from gripping the work members. For example, finger grippers may be attached to a motor and encoder on a separate mechanism for operation by the other hand of the surgeon. Alternatively, finger grippers may be attached to a motor and encoder on the same device for operation by the surgeon.

When employing telesurgery system 10 for laparoscopic surgery, positioning mechanism 14 is mounted to a manually-operated setup joint (not shown). After the setup joint has been used to position the tool and lock the tool in place, the surgeon then manipulates master device 150 to move instrument 12 through a cannula 113 inserted through small incision 112 in the abdominal wall 110 of the patient. In response to manipulation of master device 150, the distal portion 28b of the instrument 12 is translated downwardly relative to positioning mechanism 14 along sliding joint 30 for insertion through cannula 113 and abdominal wall 110.

Figure 2:
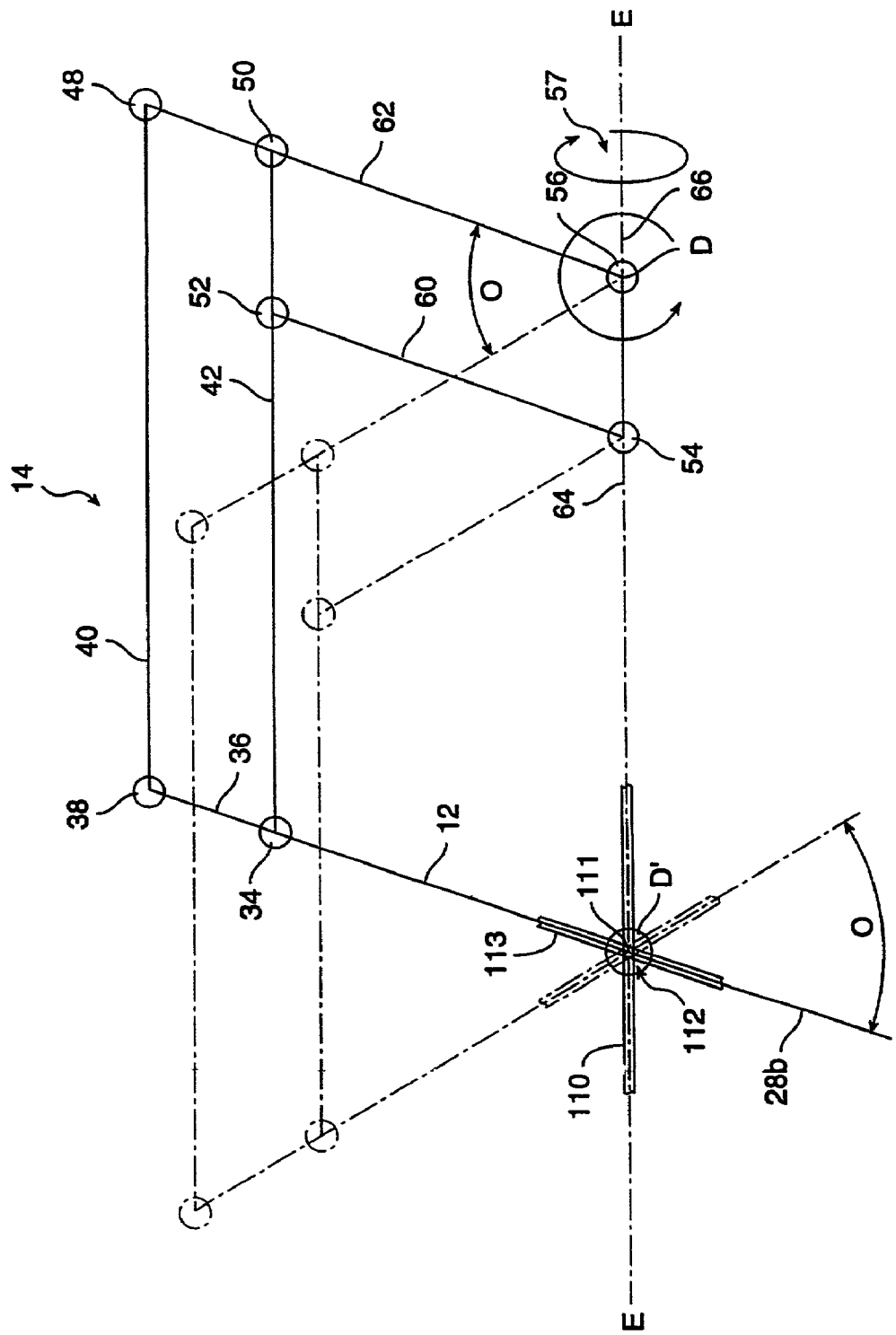
FIG. 2 is a schematic drawing of a positioning mechanism in forward and rearward positions with the surgical instrument inserted into a patient.

Once within the abdomen, the distal portion 28b of instrument 12 is further positioned over the desired surgical site. FIG. 2 depicts motion of mechanism 14 pivoted about axis D—D in forward and rearward positions for making large position movements. Positioning mechanism 14 pivots about axes D—D and E—E to perform large movements of telesurgery system 10 while precise movements are made by the joints of instrument 12. Point 111 on instrument 12 is a remote point of rotation from positioning mechanism 14 which coincides with entry wound 112. When positioning mechanism 14 is pivoted about axes D and E, instrument 12 pivots about point 111. Note that point 111 adjacent incision 112 remains stationary as the instrument 12 is pivoted within the patient. As a result, incision 112 only needs to be large enough to accept instrument 12.

As positioning mechanism 14 pivots, if wrist member 22 or work members 20a/20b engage tissue causing rotation about joints 16 or 19a/19b, instrument 12 will reorient itself so that instrument 12 is maintained relative to positioning mechanism 14 in the middle of its workspace. If necessary, positioning mechanism 14 can slow down as instrument 12 is reorienting itself.

Once instrument 12 is in the proper position, by further manipulating master device 150, the surgeon can perform the necessary surgical procedures on the patient with instrument 12. Forces experienced by instrument 12 are reflected back to the surgeon by master device 150. The reflected forces may be scaled up in order to allow the surgeon to better "feel" the surgical procedures. As a result, the surgeon can feel instrument 12 engaging types of tissue that do not provide much resistance. In addition, movements of master device 150 relative to instrument 12 may be scaled down so that the precision and dexterity of instrument 12 can be increased.

Positioning mechanism 14, because it is optimized to have a large range of motion, is likely to have higher inertia, higher friction and lower resolution than instrument 12. Moreover, friction forces in cannula 113 and disturbance forces at incision 112 may be applied to the positioning mechanism. However, in applicants' preferred embodiment, primarily the surgical instrument detects forces for force reflection. Therefore, the higher inertia and friction of the positioning mechanism and the extraneous forces acting on it are excluded from the force reflection system. Thus, the quality of the force reflection between the tip of the instrument 12 and the master device is greatly improved.

Figure 3:
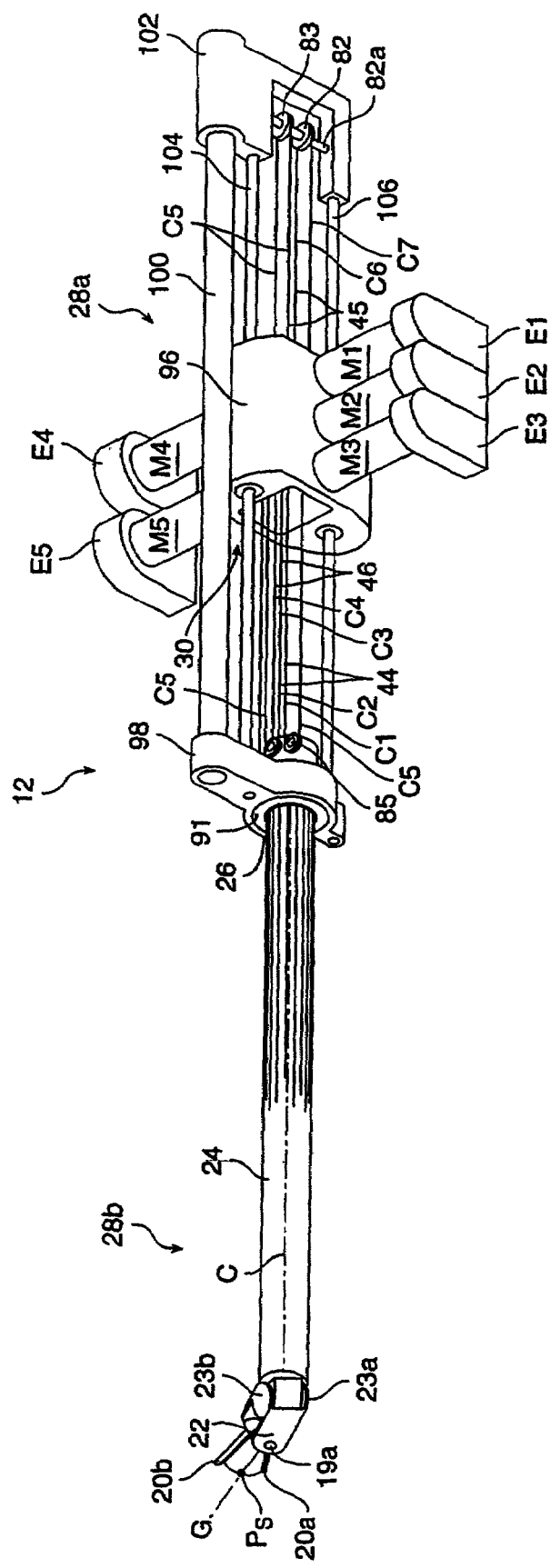
FIG. 3 is a perspective view of a force-reflecting surgical instrument.
Figure 4:
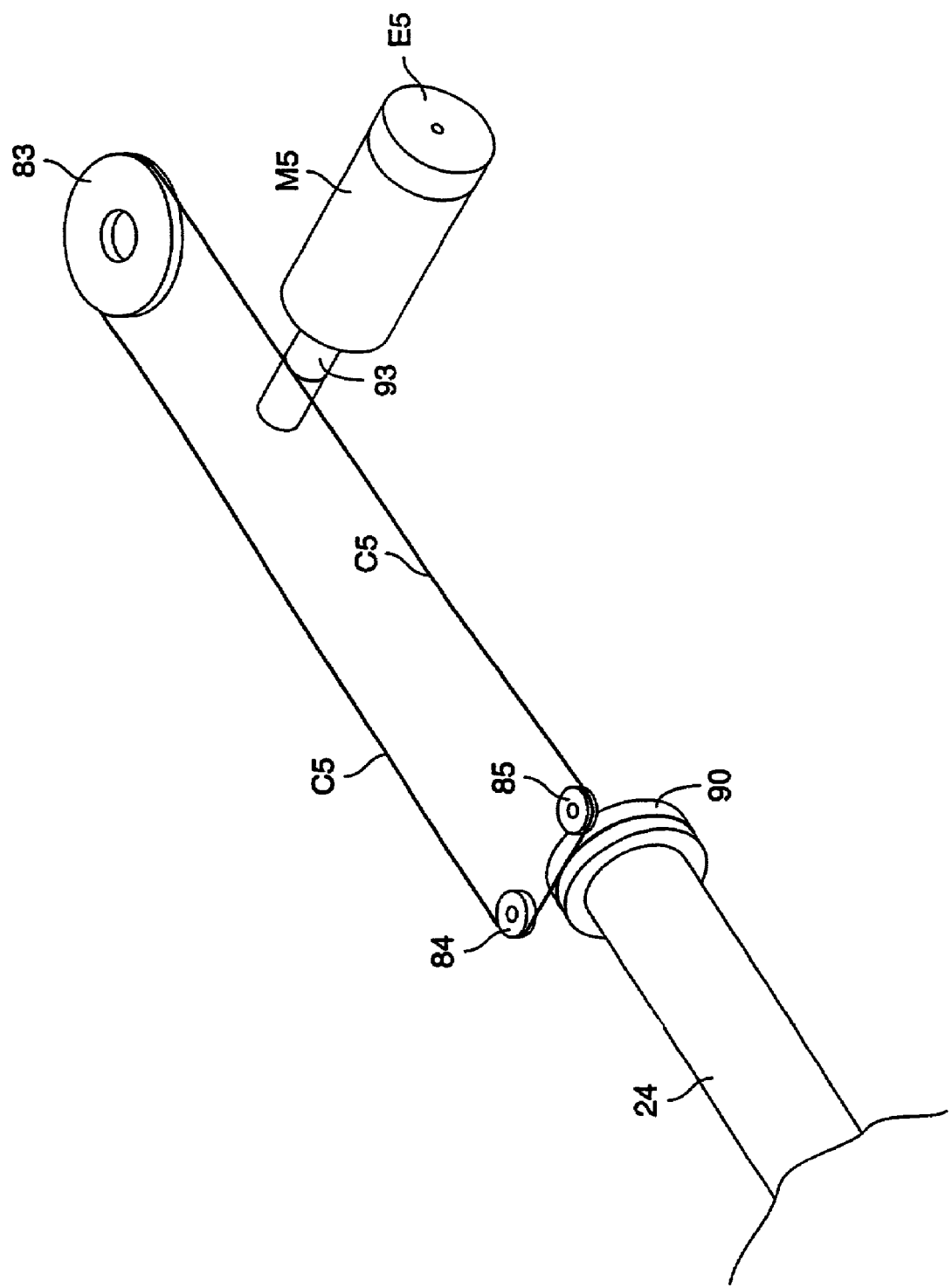
FIG. 4 is a schematic view of the cable drive actuation of the rotary motion of the force-reflecting surgical instrument.
Figure 5:
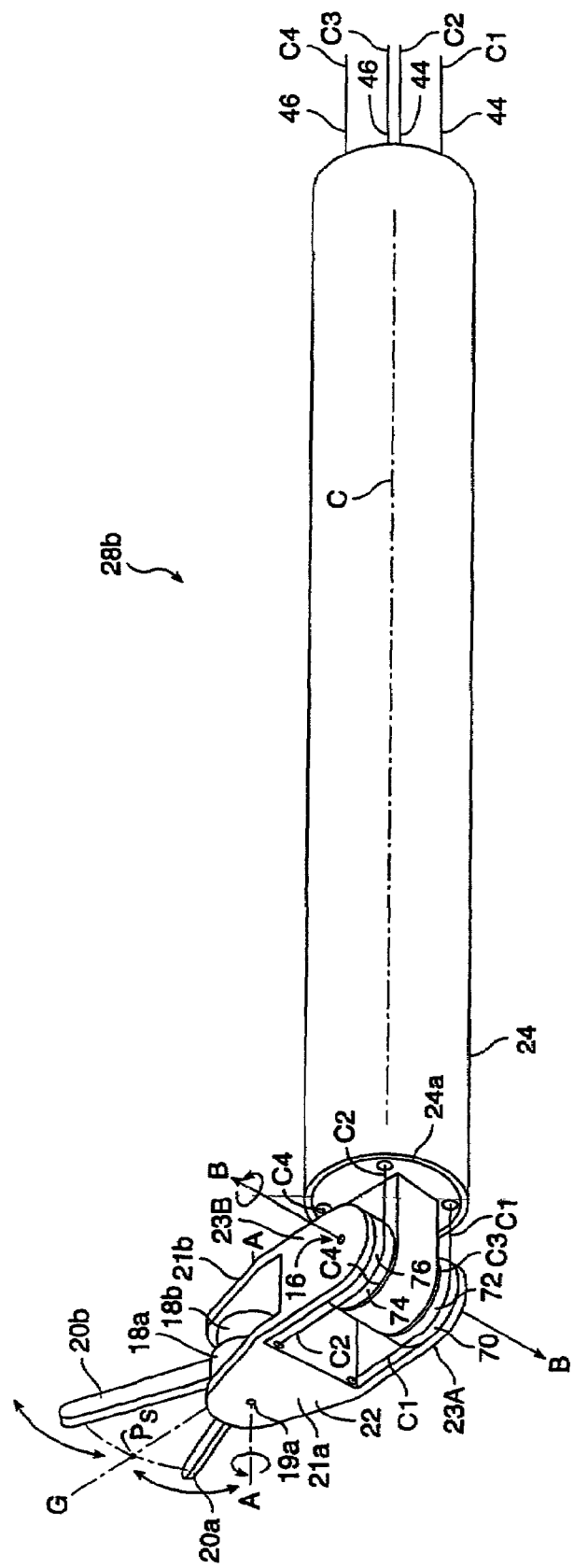
FIG. 5 is a perspective view of the distal end of the force-reflecting surgical instrument.

Referring to FIGS. 3, 4 and 5, instrument 12 is now described in greater detail. Tubular support member 24 of distal portion lies along axis C—C and houses a series of cables C1, C2, C3 and C4 which travel the length of tubular support member 24. Cables C1, C2, C3 and C4 control the rotation of joints 19a, 19b and 16 for controlling the operation of work members 20a and 20b and the orientation of wrist member 22. Wrist member 22 includes two opposed distal ears 21a and 21b forming a clevis for supporting driven capstans 18a and 18b at respective capstan joints 19a and 19b which lie along axis A—A. Wrist member 22 also includes two opposed proximal ears 23a and 23b forming a clevis for supporting intermediate idler pulleys 70 and 72 which lie along axis B—B between ear 23a and tongue 24a at wrist joint 16. Intermediate idler pulleys 74 and 76 are supported between ear 23b and tongue 24a. Cables C1, C2, C3 and C4 engage driven capstans 18a/18b as well as intermediate idler pulleys 70, 72, 74 and 76 as described later in greater detail.

Work members 20a and 20b may be removably fixed to respective driven capstans 18a and 18b. Although work members 20a and 20b are depicted in the figures as being grippers, work members 20a and 20b can be replaced with other types of work members such as scissors, cutters, graspers, forceps or needle holders for stitching sutures. Typically, the work members are fixed to driven capstans 18a and 18b by a screw, clip or other suitable fastener. However, the work members may also be permanently affixed to the driven capstans by soldering or welding, or the like, or may be formed in one piece with the driven capstans.

Work members 20a and 20b together comprise one form of surgical end effector. Other surgical end effectors may be used in the surgical instrument of the present invention. End effectors simply may comprise standard surgical or endoscopic instruments with their handles removed including, for example, retractors, electrocautery instruments, microforceps, microneedle holders, dissecting scissors, blades, irrigators, and sutures. The end effectors will typically comprise one or two work members.

Proximal portion 28a of instrument 12 includes support brackets 98 and 102 which are connected together by a support rod 100 as well as two guide rails 104 and 106. A rotary bearing 91 forming rotary joint 26 is housed within support bracket 98 for supporting tubular support member 24. Sliding bracket 96 is slidably mounted to guide rails 104 and 106 along linear bearings. As shown in FIG. 1, sliding bracket 96 is connected by bracket 36 to positioning mechanism 14. Sliding bracket 96 preferably has about 8 inches of travel for surgical applications.

Drive motors M1, M2, M3, M4 and M5 are mounted to sliding bracket 96 and drive respective cables C1, C2, C3 and C4 and C5. Sliding bracket 96 supports each of the drive motors. During operation sliding bracket 96 is connected to positioning mechanism 14 by mounting bracket 36. When instrument 12 is mounted on positioning mechanism 14, the drive motors operate to move distal portion 28b relative to sliding bracket 96. Sliding bracket 96 thus forms the support bracket of the surgical instrument. Each drive motor M1, M2, M3, M4 and M5 includes a respective encoder E1, E2, E3, E4 and E5 for providing computer 11 with the rotational position of their respective drive shafts.

As shown in FIG. 4, drive motor M5 has a drive shaft capstan 93 which engages a cable drive loop consisting of Cable C5. The cable passes around rear tensioning pulley 83. The cable passes around idler pulleys 84 and 85 and around drive capstan 90 which forms the proximal end of tubular support member 24. Thus rotation of actuation of motor M5 can be used to rotate tubular support member 24 and the end effector it supports.

Figure 6:
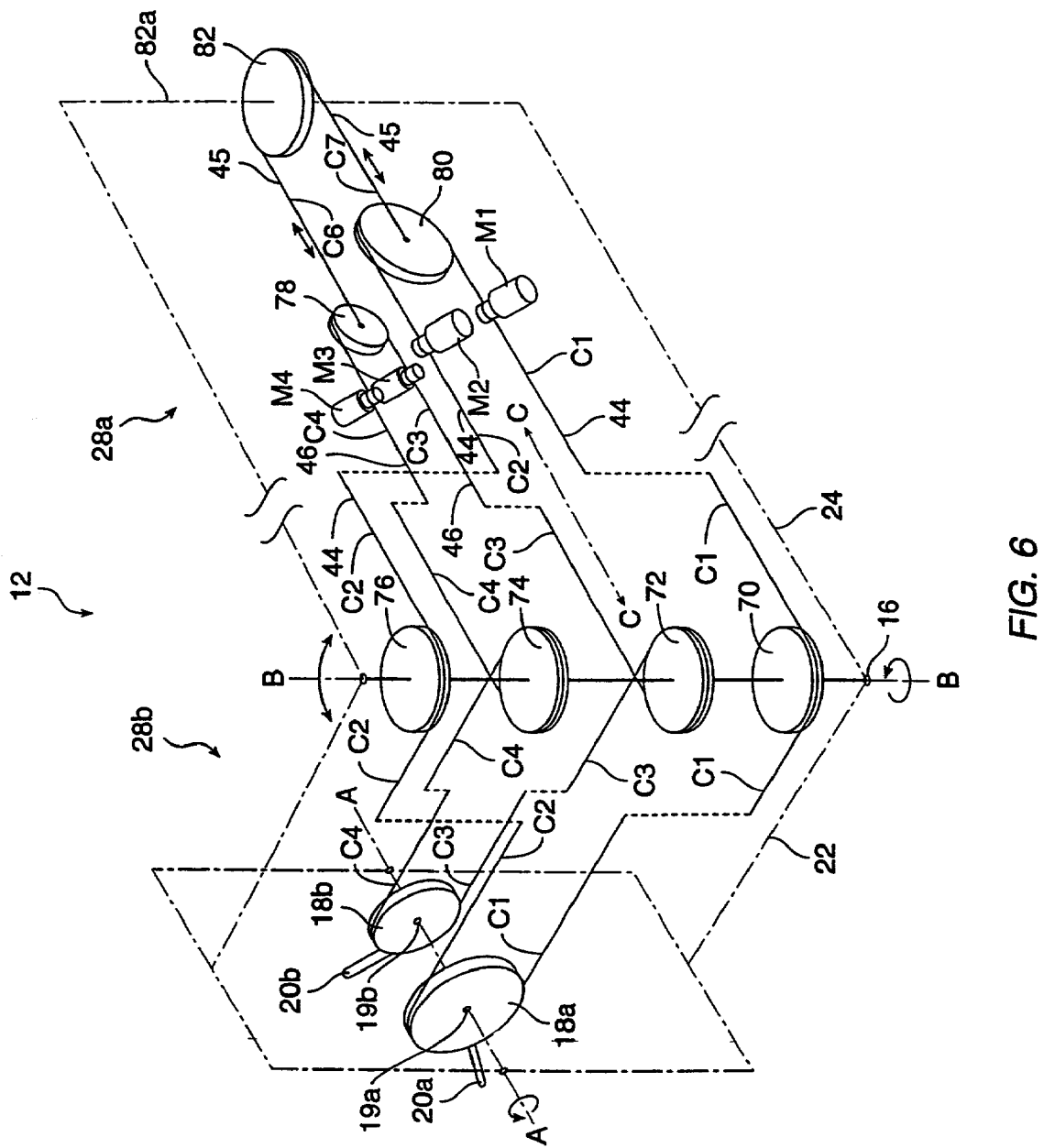
FIG. 6 is a simplified schematic drawing of the force-reflecting surgical instrument showing the relationship of the cables and pulleys.

Referring to FIG. 6, the cable drive system of instrument 12 is now described in greater detail. Work members 20a and 20b, wrist member 22 and the translation of instrument 12 along longitudinal axis C—C are driven by cables C1, C2, C3 and C4 which are arranged in an N+1 actuation scheme. The N+1 actuation scheme allows the actuation of a three degree-of-freedom wrist using four cables. Four cables is the theoretical minimum possible number of tension elements required to drive three degrees-of-freedom and thus allows the instrument to be of minimum size and weight. Alternative actuation schemes using more cables may be desirable in situations where the forces required for actuation of different motions differ greatly in magnitude. The disadvantage of using more cables is an increase in weight, complexity and minimum size.

In FIG. 6, the rotational motion of joint 26 about axis C—C is omitted in order to more easily show cables C1–C4. Such rotation results only in twisting of the cables C1–C4 between motors M1–M4 and pulleys 70, 72, 74 and 76. The cables are however arranged in tubular support member 24 such that this twisting does not significantly change the length of the cable path. Care should however be taken to prevent over-rotation of the instrument which would cause the cables to twist into contact with each other and create friction between the cables.

As shown in FIG. 6, cables C1 and C2 form two sides of a continuous cable loop 44. Cable C1 of loop 44 engages a proximal idler pulley 80, the drive shaft of motor M1, intermediate idler pulley 70 and driven capstan 18a. Cable loop 44 returns from driven capstan 18a as cable C2 and engages intermediate idler pulley 76, the S drive shaft of motor M2 and proximal idler pulley 80.

As shown in FIG. 6. cables C3 and C4 form two sides of a continuous loop of cable 46. Cable C3 of cable loop 46 engages proximal idler pulley 78, the drive shaft of motor M3. intermediate idler pulley 72 and driven capstan 18b. Cable loop 46 returns from driven capstan 18b as cable C4 and engages intermediate idler pulley 74, the drive shaft of motor M4 and proximal idler pulley 78.

As shown in FIG. 6, proximal idler pulleys 78 and 80 are tensioned by cables C7 and C6 which are fixed to the center of proximal idler pulleys 78 and 80. Cables C7 and C6 form two sides of a single cable 45 which engages proximal idler pulley 82 which is rotatably mounted to support bracket 102 by shaft 82a. Shaft 82a is preferably movably mounted to support bracket 102 by a mechanism such as a lead screw. The lead screw may then be adjusted to appropriately tension cables C7 and C6. The tension is also applied via idler pulleys 78 and 80 to cables C1, C2, C3 and C4. A similar lead screw tensioning scheme can be used to tension cable C5 by longitudinal movement of idler pulley 83. It may be required for idler pulleys 82 and 83 to be mounted on separately adjustable shafts for these purpose instead of single shaft 82a illustrated in FIG. 3.

Driven capstans 18a and 18b may have different diameters in order to allow cables C1 through C4 to suitably engage their respective intermediate idler pulleys. Cables C1 and C2 engage the outer intermediate idler pulleys 70 and 76 while cables C3 and C4 engage the inner intermediate idler pulleys 72 and 74. Proximal idler pulleys 78 and 80 are sized such that pulley 80 is larger than pulley 78 to keep the cables straight.

Drive motors M1, M2, M3 and M4 control rotation of wrist member 22 about axis B—B, translation of instrument 12 longitudinally along axis C—C and rotation of work members 22a and 22b independent of each other about axis A—A by driving cables C1, C2, C3 C3/C4 driven by drive motors M3 and M4 in order to rotate wrist member 22 about axis B—B. Drive motor M1 drives cable C1 in opposition to cable C2 driven by drive motor M2 to rotate capstan 18a and attached work member 20a about axis A—A. In addition, drive motor M3 drives cable C3 in opposition to cable C4 driven by drive motor M4 to rotate capstan 18b and attached work member 20b about axis A—A. All four drive motors M1, M2, M3 and M4 drive cables C1, C2, C3 and C4 simultaneously to translate instrument 12 along longitudinal axis C—C.

Locating drive motors M1, M2, M3, M4 and M5 on sliding bracket 96 makes the distal portion 28b of instrument 12 have a small moving mass since the motors themselves remain stationary during actuation of the instrument. Although the motors are moved by positioning mechanism 14, the weight and inertia of the motors do not affect force reflection. This is because, as stated above, in the preferred embodiment, only the instrument is used to reflect forces to the master. In addition, employing cables instead of gears to control instrument 12 minimizes the amount of friction and backlash within instrument 12. The combination of small moving masses and low friction enables instrument 12 to provide force reflection to master device 150 with high sensitivity.

Certain possible changes to the configuration of pulleys, cables and motors described above will be apparent to those of skill in the art. Although cables C1/C2, C3/C4, C5 and C7/C6 have been depicted to be sides of the same cables, cables C1–C7 alternatively can each be individual cables which are fixed to driven capstans 18a and 18b, and proximal idler pulleys 78, 80 and 82. Moreover, although drive motors M1, M2, M3 and M4 have been depicted to drive cables C1, C2, C3 and C4 respectively, alternatively, some drive motors can be relocated from cables C1-C4 onto cables C7 and C6 for driving cables C7 and C6. The choice of the particular drive scheme employed in a particular embodiment will depend on the constraints of the forces required to be exerted by the instrument and the need to reduce the inertia and friction of the parts of the instrument that move during its actuation.

The surgical instrument of the present invention has been illustrated as using drive motors M1, M2, M3, M4 and M5. This drive motors may be standard servo motors having position encoders as shown in FIG. 3. However, other actuators may be used, such as hydraulic actuators and piezoelectric motors. To be used as an actuator in the present surgical instrument a drive mechanism should be able to provide variable and controllable force and position control.

Cables C1, C2, C3, C4, C7, C8 and C9 are driven by being wrapped about the drive shaft of their respective drive motors M1, M2, M3, M4, M5, M6 and M7. This cable drive method and an alternative cable drive method are illustrated in more detail in FIGS. 7a and 7b. For example, in FIG. 7a, cable C4 of cable loop 46 is wrapped around the drive shaft of motor M4. Cable C4 is preferably wrapped two times around the drive shaft to provide enough friction between the cable C4 and the drive shaft to prevent slippage. In order to further prevent slippage the cable may be fixed to the drive shaft at one point by soldering, welding or mechanical fixing means. However, in such an embodiment the range of motion of the cable is limited by the length of cable wrapped around the drive shaft or capstan thus several turns of cable are usually required.

Figure 7A:
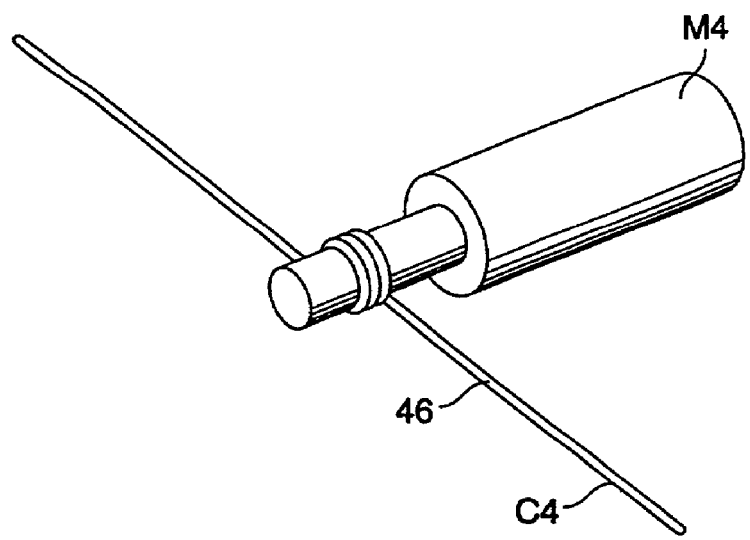
FIG. 7a is a perspective view of a cable wrapped around the drive shaft of a drive motor.
Figure 7B:
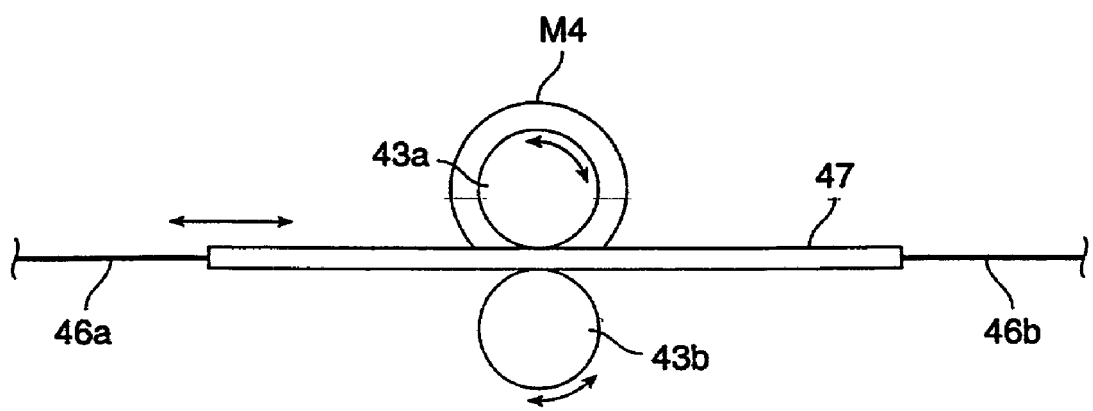
FIG. 7b is a schematic drawing showing another preferred method for driving the cables in the present invention.

FIG. 7b depicts another preferred method for driving cables. For example, motor M4 includes a drive wheel 43a and a idler wheel 43b for frictionally driving an elongate member 47 therebetween. Cable C4 consists of two halves, 46a and 46b which are fixed to opposite ends of member 47.

Figure 8:
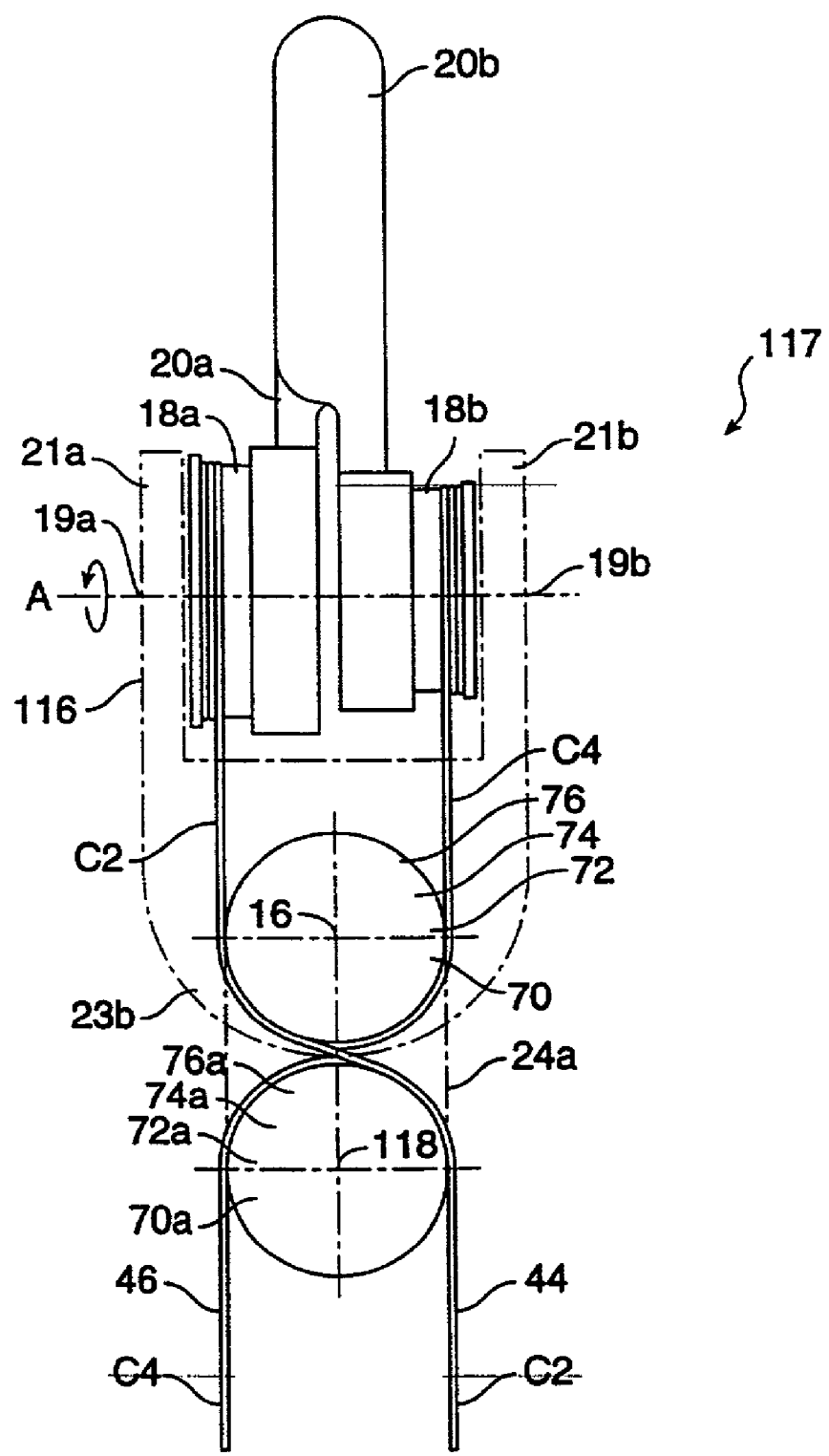
FIG. 8 is a top view of the wrist member of another preferred force-reflecting surgical instrument.

FIG. 8 depicts the distal end and wrist member 116 of another preferred instrument 117. Instrument 117 differs from instrument 12 in that instrument 117 includes eight intermediate idler pulleys instead of four. Instrument 117 includes intermediate idler pulleys 76, 74, 72 and 70 at wrist joint 16 but also includes intermediate idler pulleys 76a, 74a, 72a and 70a which are positioned adjacent to idler pulleys 76, 74, 72 and 70 on tongue 24a along shaft 118. Cables C1, C2, C3 and C4 do not make a complete wrap around each intermediate idler pulley but instead contacts a variable amount of the surface of each pulley varying in a range between 0° and 180° over the range of motion of the wrist about axis 16. This prevents the cables from crossing each other and rubbing together which prevents friction and noise.

Although the present invention has been described for performing laparoscopic surgery, it may also be used for other forms of endoscopic surgery as well as open surgery. The present manipulator could also be employed for any suitable remote controlled application requiring a dexterous manipulator with high quality force feedback. Moreover, while this invention has been particularly shown and described with references to preferred embodiments thereof, it will be understood by those skilled in the art that various changes in form and details may be made therein without departing from the spirit and scope of the invention as defined by the appended claims.

What is claimed is:

1. An articulated instrument for minimally invasive surgery, comprising:
   an elongate support member having a proximal portion and a distal end with a longitudinal axis therebetween;
   a pivotal wrist member coupled to the distal end of the elongate support by a wrist joint; and
   a surgical end effector coupled to the wrist member by at least one joint, the end effector including at least one pair of work members pivotally coupled to the wrist member, wherein at least one work member can pivot relative to the other work member of the pair, and wherein at least one work member is removably fixed to the wrist member,
   said articulated instrument having a size and shape suitable for distal insertion into an internal surgical site through an aperture.

2. The articulated instrument of claim 1, further comprising at least one wrist drive element coupled to the wrist member and adapted for coupling to at least one actuator for pivoting the wrist member about the wrist joint.

3. The articulated instrument of claim 2, wherein the wrist drive element includes a cable.

4. The articulated instrument of claim 1, further comprising at least one end effector drive element coupled to at least one end effector work member and adapted for coupling to at least one actuator for pivoting the work member relative to the wrist member.

5. The articulated instrument of claim 4, wherein the end effector includes at least one pivotally-mounted capstan coupled to the end effector drive element, and the at least one end effector work member is removably fixed to the capstan.

6. The articulated instrument of claim 5, wherein the end effector drive element includes a cable.

7. The articulated instrument of claim 1, wherein one of said work members is pivotally connected to the other work member, and both work members are pivotally connected to the wrist member.

8. The articulated instrument of claim 1, wherein the at least one end effector work member is removably fixed to the wrist member by at least one of a screw and a clip.

9. The articulated instrument of claim 1, wherein the end effector comprises a gripper, a scissors, a cutter, a graspers, a forceps, a needle holder, a retractor, an electrocautery instrument, a microforceps, a microneedle holder, a dissecting tool, a blade, or an irrigator, or a combination of these.

10. The articulated instrument of claim 1, further comprising at least one substitute member adapted to be removably fixed to the wrist member to replace the at least one removably fixed work member.

11. The articulated instrument of claim 10, wherein the substitute member is of a different surgical type than the at least one removably fixed work member.

12. A minimally invasive surgical system including:
   an arm having a proximal end portion adapted to be attached to a base so as to permit a distal end portion of the arm to move relative to the base; and
   an articulated surgical instrument mounted on the distal end of the arm, the instrument comprising:
      an elongate support member having a proximal portion and a distal end with a longitudinal axis therebetween,
      a pivotal wrist member coupled to the distal end of the elongate support member by a wrist joint, and
      at least one surgical end effector work member coupled to the wrist member by at least one joint, the work member comprising an electrocautery instrument being removably fixed to the wrist members,
      said articulated surgical instrument having a size and shape suitable for distal insertion into an internal surgical site through an aperture.

13. The surgical system of claim 12, further comprising a drive system including at least one wrist drive element coupled to the wrist member and adapted for coupling to at least one actuator for pivoting the wrist member about a wrist joint.

14. The surgical system of claim 13, wherein the wrist drive element includes a cable.

15. The surgical system of claim 12, wherein the at least one end effector work member includes at least a pair of work members pivotally coupled to the wrist member, wherein at least one work member can pivot relative to the other work member of the pair.

16. The surgical system of claim 15, further comprising at least one end effector drive element coupled to at least one end effector work member and adapted for coupling to at least one actuator for pivoting the work member relative to the wrist member.

17. The surgical system of claim 16, further comprising at least one pivotally-mounted capstan coupled to the end effector drive element, and the at least one end effector work member is removably fixed to the capstan.

18. The surgical system of claim 17, wherein the end effector drive element includes a cable.

19. The surgical system of claim 15, wherein one of said work members is pivotally connected to the other work member, and both work members are pivotally connected to the wrist member.

20. The surgical system of claim 12, wherein the at least one end effector work member is removably fixed to the wrist member by at least one of a screw and a clip.

21. The surgical system of claim 12, further comprising at least one substitute member adapted to be removably fixed to the wrist member to replace the at least one end effector work member.

22. The articulated instrument of claim 21, wherein the substitute member is of a different surgical type than the at least one end effector work member.

23. A method for minimally invasive surgery in a patient, comprising:
   (a) providing an articulated surgical instrument including:
      an elongate support member having a proximal portion and a distal end with a longitudinal axis therebetween;
      a pivotal wrist member coupled to the distal end of the elongate support member by a wrist joint; and
      a surgical end effector coupled to the wrist member by at least one joint, the end effector including at least one pair of work members pivotally coupled to the wrist member, wherein at least one work member can pivot relative to the other work member of the pair, and wherein at least one work member is removably fixed to the wrist member,
      said articulated surgical instrument having a size and shape suitable for distal insertion into an internal surgical site through an aperture;
   (b) inserting a distal portion of the surgical instrument through an aperture in a patient's body to a location adjacent a surgical worksite, the distal portion including at least the wrist member and the end effector;
   (c) performing a surgical treatment using the at least one end effector work member;
   (d) removing the at least one end effector work member from the wrist member;
   (e) providing a substitute member;
   (f) replacing the at least one end effector work member by removably fixing the substitute member to the wrist member; and
   (g) performing a surgical treatment using the substitute member.

24. The method of claim 23, further comprising the steps of:
   (h) prior to the removing step (d), retracting the distal portion from the aperture in the patient's body; and
   (i) following the replacing step (f), inserting the distal portion of the surgical instrument through an aperture in a patient's body to a location adjacent a surgical worksite.

25. The method of claim 23, further comprising the step of:
   (j) moving the wrist member to position the end effector for surgical treatment.

26. The method of claim 25, wherein:
   the articulated instrument provided in step (a) further includes at least one wrist drive element coupled to the wrist member and adapted for coupling to at least one actuator for pivoting the wrist member about the wrist joint; and
   the moving step (j) includes actuating the wrist drive element to move the wrist member.

27. The method of claim 26, wherein the wrist drive element includes a cable.

28. The method of claim 23, wherein:
   the articulated instrument provided in step (a) further includes at least one end effector drive element coupled to at least one end effector work member and adapted for coupling to at least one actuator for pivoting the work member relative to the wrist member; and
   at least one of the treatment performing steps (c) and (g) includes actuating the end effector drive element to pivot the at least one end effector work member.

29. The method of claim 28, wherein the end effector includes at least one pivotally-mounted capstan coupled to the end effector drive element, and the at least one end effector work member is removably fixed to the capstan.

30. The method of claim 29, wherein the end effector drive element includes a cable.

31. The method of claim 23, wherein the at least one end effector work member of the articulated instrument provided in step (a) is removably fixed to the wrist member by at least one of a screw and a clip.

32. The method of claim 23, wherein the end effector of the articulated instrument provided in step (a) comprises a gripper, a scissors, a cutter, a graspers, a forceps, a needle holder, a retractor, an electrocautery instrument, a microforceps, a microneedle holder, a dissecting tool, a blade or an irrigator, or a combination of these.

33. The method of claim 23, wherein the substitute member provided in step (e) is a different surgical instrument type than the at least one end effector work member provided in step (a).

34. A minimally invasive surgical system comprising:
   a base adapted to be fixed relative to a patient's body;
   an instrument positioning mechanism;
   an articulated surgical instrument assembly; and
   an instrument drive system;
   the instrument positioning mechanism including:
      a support linkage having a proximal end and a distal end, the proximal end being coupled the base and the distal end being coupled to the articulated surgical instrument assembly;
      a positioning drive system configured to move the distal end of the support linkage so as to move the articulated surgical instrument assembly in a plurality of degrees of freedom relative to the base;
   the articulated surgical instrument assembly including:
      a proximal portion and a distal portion, and an elongate support assembly having a proximal end and a distal end with a longitudinal axis therebetween;
      a pivotal wrist joint disposed adjacent the distal end of the elongate support assembly, and
      a surgical end effector including a first end effector element coupled to the wrist joint by a first pivotal end effector joint and a second end effector element coupled to the wrist joint by a second pivotal end effector joint so that the first and second end effector elements can manipulate tissues at the worksite therebetween;
      the proximal portion of the articulated surgical instrument assembly being adapted to releasably couple to the distal end of the instrument positioning mechanism;
      the distal portion of the articulated surgical instrument assembly having a size and shape suitable for insertion through an aperture in the patient's body to extent to an internal surgical site; and the instrument drive system including:
- a plurality of actuators disposed adjacent the distal end of the positioning mechanism;
- a plurality of elongate drive elements extending longitudinally from the plurality of actuators to operatively couple to a corresponding plurality of pivotal joints adjacent the distal portion of the articulated surgical instrument assembly;
- the plurality of pivotal joints including at least the pivotal wrist joint and the first pivotal end effector joint;
- the instrument drive system being configured to move the first end effector element in a plurality of degrees of freedom relative to the distal end of the positioning mechanism.

35. The surgical system of claim 34, wherein the positioning mechanism further comprises a linear bearing coupling the articulated surgical instrument assembly to the distal end of the support linkage, to permit axial translation of the articulated surgical instrument assembly relative to the base.

36. The surgical system of claim 34, wherein the elongate drive elements are configured to hold the plurality of pivotal joints at fixed angles when the actuators do not move the elongate drive elements and the articulated surgical instrument assembly is translated axially.

37. The surgical system of claim 34, wherein the elongate elements comprise cable elements including at least one portion of cable.

38. The surgical system of claim 37, wherein the cable elements are configured to twist within the elongate support assembly so that the distal portion of the articulated surgical instrument assembly can rotate about the axis relative to the positioning mechanism and the actuators.

39. The surgical system of claim 37, wherein at least one of the plurality of cable element comprises a continuous loop.

40. The surgical system of claim 37, wherein the positioning mechanism is configured to cause the articulated surgical instrument assembly to pivot about at least a first axis relative to the base.

41. The surgical system of claim 34, wherein the instrument drive system includes a rotational connection arranged to permit the elongate support assembly to rotate about the longitudinally axis.

42. The surgical system of claim 34, wherein the end effector joints pivot about a common end effector axis, and wherein the instrument drive system can move the first and second end effector elements independently.

43. The surgical system of claim 34, wherein at least one actuator of the instrument drive system includes a rounded drive capstan engaging at least one of the plurality of elongate drive elements, so as to cause the elongate drive element to move when the capstan is rotated so as to cause the rotation of at least one of the plurality of rotary joints of the articulated surgical instrument assembly.

44. The surgical system of claim 43, wherein the elongate drive element comprises a cable element including at least one portion of cable.

45. The surgical system of claim 44, wherein the cable element comprises a continuous loop.

46. The surgical system of claim 34, wherein at least one of the plurality of elongate drive elements engages an idler pulley, so as to guide the elongate element intermediate the corresponding actuator and corresponding rotary joint.

47. The surgical system of claim 34, wherein at least one of the pivotal wrist joint and the first pivotal end effector joint includes a driven capstan portion, the driven capstan portion engaging at least one of the plurality of elongate drive elements, so as to cause the pivotal joint to rotate in response to movement of the elongate drive element.

48. The surgical system of claim 34, wherein the positioning mechanism and the instrument drive system in combination are configured to move the first end effector element in at least five degrees of freedom relative to the base.

49. The articulated instrument of claim 1, further comprising an arm having a proximal end portion adapted to be attached to a base so as to permit a distal end portion of the arm to move relative to the base, the articulated surgical instrument mounted on the distal end of the arm.

50. An articulated instrument for minimally invasive surgery, comprising:
- an elongate support member having a proximal portion and a distal end with a longitudinal axis therebetween;
- a pivotal wrist member disposed at the distal end of the elongate support member; and
- a surgical end effector pivotally coupled to the wrist member, the end effector including at least one end effector work member, the work member being removably fixed to the wrist member by at least one of a clip and a screw,
- said articulated instrument having a size and shape suitable for distal insertion into an internal surgical site through an aperture.

51. The articulated instrument of claim 50, further comprising at least one wrist drive element coupled to the wrist member and adapted for coupling to at least one actuator for pivoting the wrist member about a wrist joint.

52. The articulated instrument of claim 51, wherein the wrist drive element includes a cable.

53. The articulated instrument of claim 50, wherein the at least one end effector work member includes at least a pair of work members pivotally coupled to the wrist member, wherein at least one work member can pivot relative to the other work member of the pair.

54. The articulated instrument of claim 53, further comprising at least one end effector drive element coupled to at least one end effector work member and adapted for coupling to at least one actuator for pivoting the work member relative to the wrist member.

55. The articulated instrument of claim 54, wherein the end effector includes at least one pivotally-mounted capstan coupled to the end effector drive element, and the at least one end effector work member is removably fixed to the capstan.

56. The articulated instrument of claim 55, wherein the end effector drive element includes a cable.

57. The articulated instrument of claim 53, wherein one of said work members is pivotally connected to the other work member, and both work members are pivotally connected to the wrist member.

58. The articulated instrument of claim 50, wherein the end effector comprises a gripper, a scissors, a cutter, a graspers, a forceps, a needle holder, a retractor, an electrocautery instrument, a microforceps, a microneedle holder, a dissecting tool, a blade, or an irrigator, or a combination of these.

59. The articulated instrument of claim 50, further comprising at least one substitute member adapted to be removably fixed to the wrist member to replace the at least one removably fixed work member.

60. The articulated instrument of claim 59, wherein the substitute member is of a different surgical type than the at least one removably fixed work member.

61. A method for minimally invasive surgery in a patient, comprising:
(a) providing an articulated surgical instrument including:
an elongate support member having a proximal portion and a distal end with a longitudinal axis therebetween;
a pivotal wrist member coupled to the distal end of the elongate support member by a wrist joint; and
a surgical end effector coupled to the wrist member by at least one joint, the end effector including at least one end effector work member, the work member comprising an electrocautery instrument being removably fixed to the wrist member;
said articulated instrument having a size and shape suitable for distal insertion into an internal surgical site through an aperture.
(b) inserting a distal portion of the surgical instrument through an aperture in a patient's body to a location adjacent a surgical worksite, the distal portion including at least the wrist member and the end effector;
(c) performing a surgical treatment using the at least one end effector work member;
(d) removing the at least one end effector work member from the wrist member;
(e) providing a substitute member;
(f) replacing the at least one end effector work member by removably fixing the substitute member to the wrist member; and
(g) performing a surgical treatment using the substitute member.

62. The method of claim 61, further comprising the steps of:
(h) prior to the removing step (d), retracting the distal portion from the aperture in the patient's body; and
(i) following the replacing step (f), inserting the distal portion of the surgical instrument through an aperture in a patient's body to a location adjacent a surgical worksite.

63. The method of claim 61, further comprising the step of:
(j) moving the wrist member to position the end effector for surgical treatment.

64. The method of claim 63, wherein:
the articulated instrument provided in step (a) further includes at least one wrist drive element coupled to the wrist member and adapted for coupling to at least one actuator for pivoting the wrist member about the wrist joint; and
the moving step (j) includes actuating the wrist drive element to move the wrist member.

65. The method of claim 64, wherein the wrist drive element includes a cable.

66. The method of claim 61, wherein:
the articulated instrument provided in step (a) further includes at least one end effector drive element coupled to at least one end effector work member and adapted for coupling to at least one actuator for pivoting the work member relative to the wrist member; and
at least one of the treatment performing steps (c) and (g) includes actuating the end effector drive element to pivot the at least one end effector work member.

67. The method of claim 66, wherein the end effector includes at least one pivotally-mounted capstan coupled to the end effector drive element, and the at least one end effector work member is removably fixed to the capstan.

68. The method of claim 67, wherein the end effector drive element includes a cable.

69. The method of claim 61, wherein the at least one end effector work member of the articulated instrument provided in step (a) is removably fixed to the wrist member by at least one of a screw and a clip.

70. The method of claim 61, wherein the substitute member provided in step (e) is a different surgical instrument type than the at least one end effector work member provided in step (a).

71. A method for performing a surgical procedure with a robotic surgical system comprising:
providing a surgical instrument assembly comprising a shaft with a proximal end and a distal end, a pivotal wrist member coupled to the distal end of the shaft by a wrist joint and an instrument coupled to the wrist member by at least one joint;
connecting the proximal end of the shaft of the surgical instrument assembly to a manipulator arm;
positioning the manipulator arm by articulating a mounting joint prior to surgery;
introducing the instrument of the surgical instrument assembly to a treatment site on a patient with the manipulator arm; and
moving the instrument assembly with the manipulator arm so as to perform a surgical procedure with the instrument.

72. The method of claim 71, further comprising fixing the orientation of the mounting joint during the surgical procedure.

73. The method of claim 71, further comprising removing the instrument of the surgical instrument assembly from the treatment site and disconnecting the proximal end of the shaft of the surgical instrument assembly from the manipulator arm.

74. The method of claim 73, further comprising connecting a proximal end of a wrist unit shaft of a second surgical instrument assembly to the manipulator arm, and introducing an instrument of the second surgical instrument assembly to the treatment site with the manipulator arm.

75. The method of claim 71, further comprising pivoting the instrument about at least one of the wrist joint and the at least one joint of the shaft.

* * * * *